(12) United States Patent
Kingsmore et al.

(10) Patent No.: US 6,670,126 B2
(45) Date of Patent: *Dec. 30, 2003

(54) POLY-PRIMED AMPLIFICATION OF NUCLEIC ACID SEQUENCES

(75) Inventors: Stephen Kingsmore, Guilford, CT (US); R. Steven Wiltshire, Plantsville, CT (US); Jeremy P. Lambert, Branford, CT (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/897,665

(22) Filed: Jul. 2, 2001

(65) Prior Publication Data

US 2001/0041340 A1 Nov. 15, 2001

Related U.S. Application Data

(63) Continuation of application No. 09/577,444, filed on May 24, 2000, now Pat. No. 6,291,187.
(60) Provisional application No. 60/204,057, filed on May 12, 2000.

(51) Int. Cl.[7] ............................ C12Q 1/68; C12P 19/34; C07H 21/04; C07H 21/02; C07H 19/04

(52) U.S. Cl. ...................... 435/6; 435/91.1; 435/91.2; 935/77; 935/78; 935/76; 536/23.1; 536/24.3; 536/25.32; 536/26.6

(58) Field of Search ............................ 435/6, 91.1, 91.2; 935/77, 76, 78; 536/23.1, 24.3, 25.32, 26.6

(56) References Cited

U.S. PATENT DOCUMENTS 6,143,495 A * 11/2000 Lizardi et al. ................ 435/6
6,291,187 B1 * 9/2001 Kingsmore et al. ........... 435/6

FOREIGN PATENT DOCUMENTS

WO          92/01813    * 2/1992 ............ C12Q/1/68
WO          WO 97/19193    5/1997

* cited by examiner

*Primary Examiner*—Ethan Whisenant
*Assistant Examiner*—Joyce Tung
(74) *Attorney, Agent, or Firm*—E. M. Olstein; A. J. Grant

(57) ABSTRACT

Methods for the amplification of selected nucleic acids at high rate but with high specificity and control are disclosed using a secondary, tertiary, quaternary or higher order platform especially designed to amplify selected sequences within the primary product of linear or exponential rolling circle amplification and amplifying said sequences along with specialized detector or reporter molecules that serve to enhance the ability to detect the amplification products.

43 Claims, 6 Drawing Sheets

FIG. 1(b)
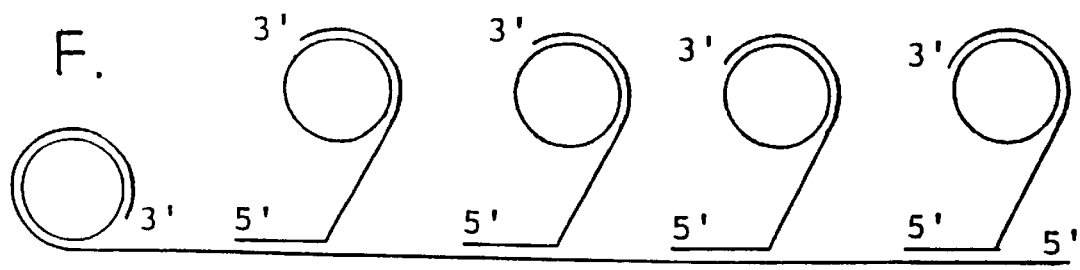
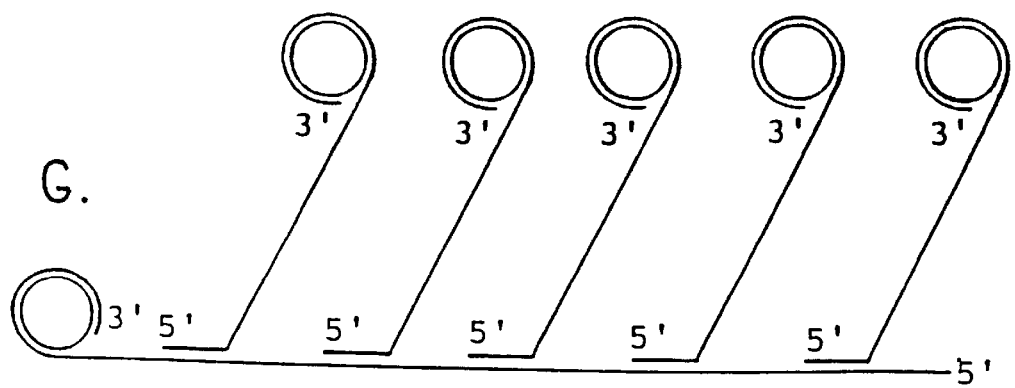

F I G. 5
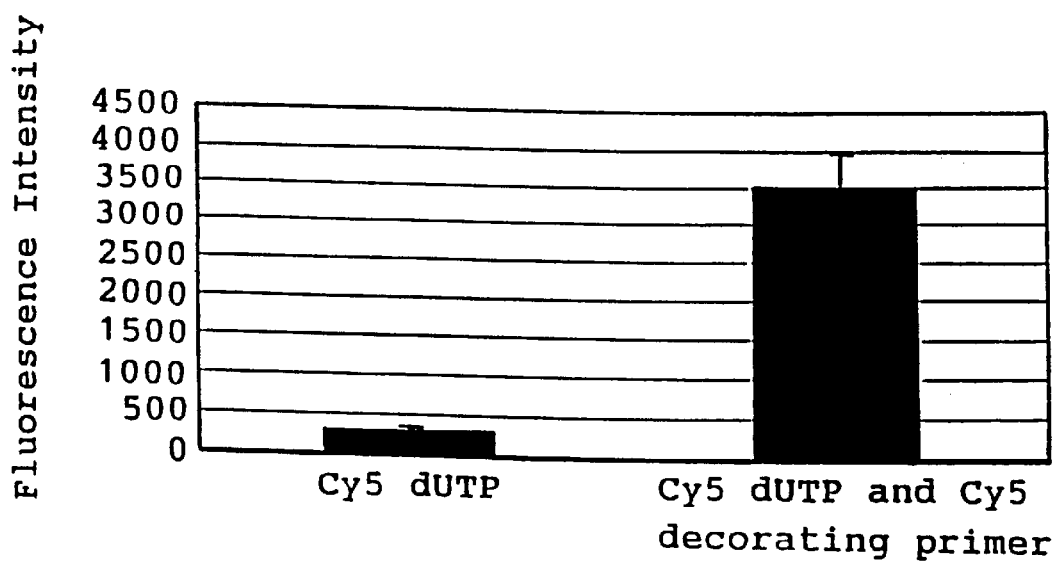

POLY-PRIMED AMPLIFICATION OF NUCLEIC ACID SEQUENCES

This application is a continuation of 09/577,444 filed May 24, 2000, now U.S. Pat. No. 6,291,187 which claims the benefit of U.S. Provisional Application 60/204,057, filed May 12, 2000, the disclosure of which is incorporated herein in its entirety.

FIELD OF THE INVENTION

The present invention relates to processes for establishing multi-tier platforms in rolling circle amplification so as to provide enhanced detection of product species with quantitative and kinetic advantages over previous rolling circle methods.

BACKGROUND OF THE INVENTION

A means of amplifying circular target DNA molecules is of value because such amplified DNA is frequently used in subsequent methods including DNA sequencing, cloning, mapping, genotyping, generation of probes, and diagnostic identification.

Heretofore, several useful methods have been developed that permit sensitive diagnostic assays based on detection of nucleic acids. Most are designed around the amplification of selected targets and/or probes composed of DNA, including the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, Trends Genetics, 9:199–202 (1993)). Some of these methods suffer from relatively low precision in quantitative measurements, especially noticeable in multiplex assays (where more than one target is to be assayed simultaneously). These shortcomings have been largely overcome by rolling circle amplification (RCA) methods.

Previously, several methods have been employed to amplify circular DNA molecules such as plasmids or DNA from bacteriophage such as M13. One has been propagation of these molecules in suitable host strains of *E. coli*, followed by isolation of the DNA by well-established protocols (Sambrook, J., Fritsch, E. F., and Maniatis, T. Molecular Cloning, A Laboratory Manual, 1989, Cold Spring Harbor Laboratory Press, Cold Spring Harbor, N.Y.). PCR has also been a frequently used method to amplify defined sequences in DNA targets such as plasmids and DNA from bacteriophage such as M13 (PCR Protocols, 1990, Ed. M. A. Innis, D. H. Gelfand, J. J. Sninsky, Academic Press, San Diego.) Some of these methods suffer from being laborious, expensive, time-consuming, inefficient, and lacking in sensitivity.

As an improvement on these methods, linear rolling circle amplification (LRCA) uses a primer annealed to the circular target DNA molecule and DNA polymerase is added. An improvement on LRCA is the use of exponential RCA (ERCA), with additional primers that anneal to LRCA product strand. Therefore, double stranded DNA can be produced, and exponential amplification can occur via strand displacement reactions referred to a HRCA (Lizardi, P. M. et al. *Nature Genetics,* (1998) 19. 225–231).

The multiple targets of multiplexed assays may, for example, be viruses or other microorganisms. Thus, the clinical condition of a virus-infected patient may depend heavily on viral load (for example, in HIV infections) and so a means for quantitatively determining such viral load is of especial value. In such multiplex assays, it is important that measurements of different targets, such as different viruses, or different strains of virus, be accurately determined and that the ratio of different targets be a true indicator of the ratio of the target sequences. For such purposes, multiplexed, exponential nucleic acid amplification methods have often been employed, but only multiplexed rolling circle amplification has been successful in meeting many of the goals of multiplexed assay systems [See: Lizardi, U.S. Pat. No. 5,854,033 the disclosure of which is hereby incorporated by reference in its entirety].

However, there are sources of error in such methods, such as where structural differences lead to different efficiencies, for example, different events are involved for different target sequences, or differences in the rates of product strand annealing may differ for different target sequences and lead to varying rates of competition with the aforementioned priming events, the effects of having multiple ligation effects occurring simultaneously for species of differing structure and stability (which events may be magnified by repetition of the ligation reactions), and the possibility that small differences in yield from one cycle of amplification to another may be magnified exponentially to result in undesirably large differences in the ratios of the final product. RCA methods have overcome errors due to signal yields, since amplification yields are proportional to the amount of target (i.e., detection efficiency is not dependent on the availability of ample amounts of target DNA so that even minute amounts of target can provide enormous signal sensitivity).

The earliest method for DNA amplification was the polymerase chain reaction (PCR) which operated only on linear segments of DNA and produced linear segments using specific primer sequences for the 5'- and 3'-ends of a segment of DNA whose amplification was desired. As an improvement on this method, linear rolling circle amplification (LRCA) uses a target DNA sequence that hybridizes to an open circle probe to form a complex that is then ligated to yield an amplification target circle and a primer sequence and DNA polymerase is added. The amplification target circle (ATC) forms a template on which new DNA is made, thereby extending the primer sequence as a continuous sequence of repeated sequences complementary to the ATC but generating only about several thousand copies per hour. An improvement on LRCA is use of exponential RCA (ERCA) with additional priming sequences that bind to the replicated ATC-complement sequences to provide new centers of amplification, thereby providing exponential kinetics and greatly increased amplification. Exponential rolling circle amplification (ERCA) employs a cascade of strand displacement reactions but is limited to use of the initial single stranded RCA product as a template for further DNA synthesis using individual single stranded primers that attach to said product but without additional rolling circle amplification.

All of these methods suffer from a lack of sensitivity, especially to rare genetic events, such as infrequent mutations, as well as to limits on multiplexing and the availability of flexible detection procedures.

The method of the present invention (referred to herein as Poly-Primed Rolling Circle Amplification—PPRCA) avoids such disadvantages by employing a procedure that improves on the sensitivity of linear rolling circle amplification while retaining high specificity by employing true exponential amplification using additional stages, or platforms, of RCA (thereby affording greater sensitivity) while eliminating any reliance on a ligation step yet retaining the advantages of exponential RCA and the ability to amplify on a solid phase. The present invention has the advantages of being highly useful in new applications of rolling circle amplification, low cost, sensitivity to rare events, flexibility, especially in the use of detection reagents, and low risk of contamination.

BRIEF SUMMARY OF THE INVENTION

The present invention relates to a process for the selective amplification of target DNA molecules as a means of detecting differences in the genotype of said DNA molecules, including changes, or mutations, as slight as a single nucleotide (a single nucleotide polymorphism—SNP) as well as providing a quantitative measure of the relative presence of such mutations in a given sample of DNA.

The present invention further provides a method for the selective detection of target DNA molecules by selective amplification thereof using secondary, tertiary, quaternary or higher order platforms especially designed to amplify selected sequences within the primary product of linear or exponential rolling circle amplification and amplifying said sequences along with specialized detector or reporter molecules that serve to enhance the ability to detect the amplification products.

In separate embodiments, the reporter molecules useful within the methods of the present invention include such molecules as biotin, digoxigenin, hapten and mass tags or any combination of these.

In other embodiments, the present invention employs selected nucleotides, or functionally equivalent structures, to provide linkages for detectors and reporter binding molecules of different kinds, such linkages utilizing different deoxynucleoside phosphates as well as a basic nucleotides and nucleosides selectively structured and configured so as to provide an advantage in detecting the resulting rolling circle products. Reporter molecules may also include enzymes, fluorophores and various conjugates.

A further aspect of the present invention relates to a process for the enhanced amplification of circular DNA targets. It improves on the sensitivity of linear rolling circle amplification with singly-primed template circular DNA molecules.

BRIEF DESCRIPTION OF THE DRAWINGS

FIG. 5 is a graph showing the increase in LRCA signal using decorating primers (LRCA control in column 1 on left as with FIG. 3).

DETAILED SUMMARY OF THE INVENTION

The methods of the present invention provide greatly increased amplification due to secondary, tertiary, quaternary, and higher order amplification processes occurring from a primary tandem sequence (TS-DNA) product. Such a DNA is the initial or primary product of rolling circle amplification and comprises an unbroken single strand containing tandem repeats of the sequence found in the rolling circle, or amplification target circle (ATC), used as the template. Each such tandem sequence can itself serve to bind additional primers that are then replicated along the TS-DNA, each replication fork displacing the primer before it and thereby providing a kind of exponential RCA.

In the present invention, such primers are used for attachment only and, after binding to a tandem sequence DNA product, either the primary or later TS-DNA product, provide an additional sequence for attachment of additional amplification target circles that act as additional templates for a truly exponential amplification. Thus, the rate and extent of amplification is not limited to the number of primers that can bind to the initial TS-DNA product but instead proceeds in stages, with each stage, or platform, acting as a nucleus for additional stages of amplification. Thus, in accordance with the present invention, each tandem sequence present on the initial or primary TS-DNA product acts as a seed for a whole new generation of tandem sequence amplifications, and each secondary TS-DNA product formed therefrom also comprises additional seeds, ad infinitum. It is this feature, as well as others, that provides the unique sensitivity of the present invention for amplification and detection of even rare genetic occurrences, including single nucleotide polymorphisms.

In accordance with the foregoing, one embodiment of the present invention has the secondary amplification products remaining fixed to the primary RCA product, thereby providing increased amplification, as well as detection sensitivity, and decreased opportunities for contamination. In other embodiments, secondary amplifications occur simultaneously with the primary amplification reaction resulting in greater speed and economy in the number of steps required for adequate amplification. The processes of the present invention overcome the disadvantages of so-called hyperbranched RCA arising from displacement of secondary amplification strands due to polymerase read through (i.e., the displacement of subsequent primers and their newly synthesized tails by progressing replication forks.

Figure 1A:
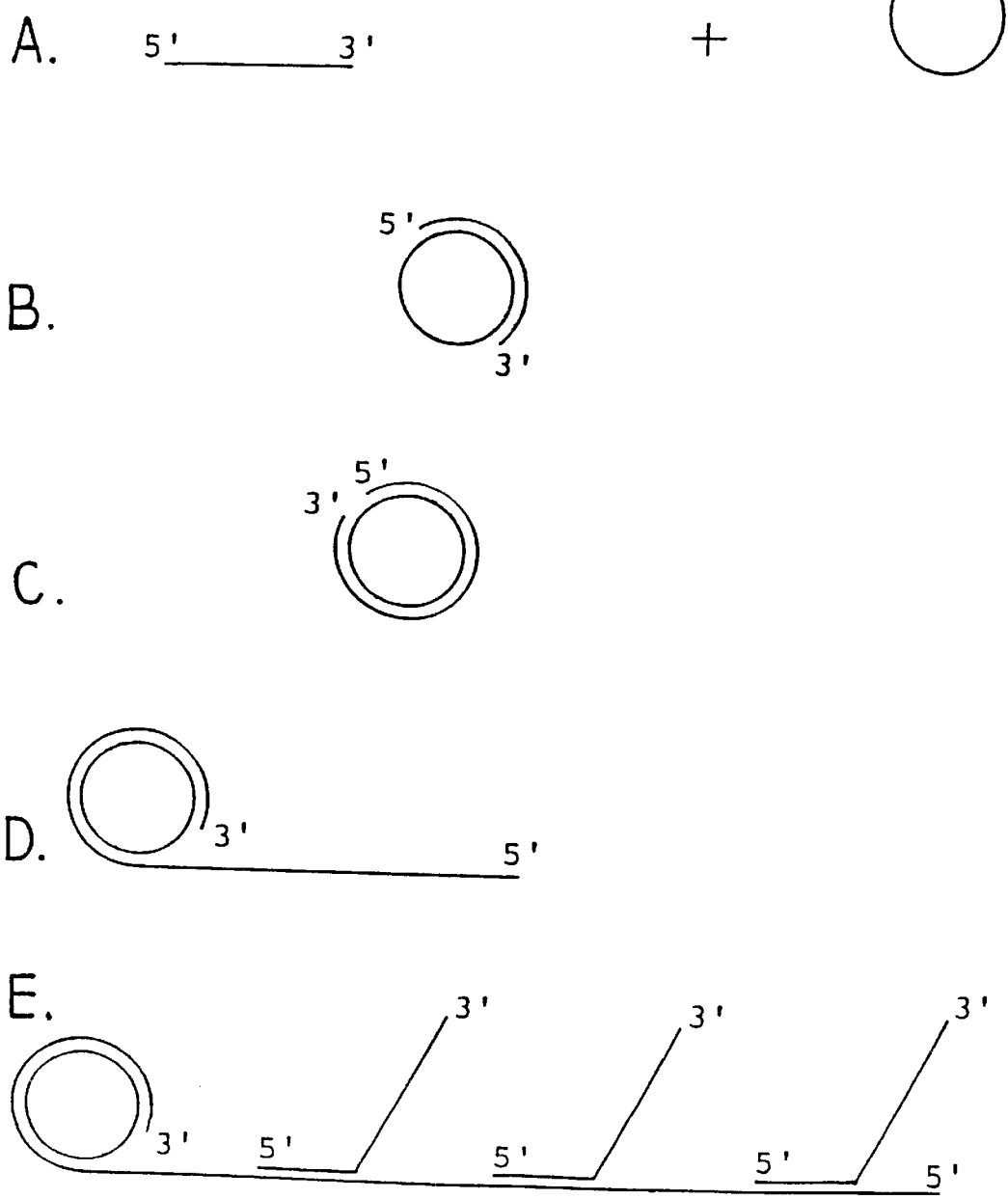
FIG. 1 shows a schematic for one embodiment of the poly-primed rolling circle amplification (PPRCA) method of the present invention. Here, an oligonucleotide primer having a region complementary to an amplification target circle (ATC) is combined with an ATC. In B, the two are allowed to hybridize with addition of enzyme, dNTPs, etc., extending the primer along the ATC as template (C). D shows extension of the RCA primer with DNA polymerase displacing the earlier segment. In E, an additional oligonucleotide primer with a region identical to the target circle and a non-complementary region hybridizes to the tandemly repeated RCA product. In F, a second amplification target circle hybridizes to primer 2 and initiates RCA from the 3'-end thereof. In G, linear RCA products are formed from the linear rolling circle scaffold, thus affording an additional level of amplification.

In currently used RCA procedures, a primer sequence, possibly bound to a target DNA sequence, is allowed to react with an additional sequence to form an amplification target circle, much as that shown in the early steps of FIG. 1 (steps A through D). However, hyperbranched chains are then formed by adding primers that bind to sequences present along the tandem sequence DNA (FIG. 1, at D). These primers initiate additional rounds of DNA synthesis by reacting with DNA polymerase to form new chains that are synthesized along the TS-DNA (as template) with each newly formed chain displacing the hybridized chain ahead of it (i.e., in the 3'-direction), the result being a long sequence of DNA as template with numerous new sequences being synthesized thereon while each such newly formed sequence is displaced at its 5'-end by the sequence being synthesized behind it. As each new segment of TS-DNA comes off of the original ATC, a new secondary primer binds to that segment and initiates a new DNA chain so that the newly formed chains increase in length as they become farther removed from the vicinity of the ATC (see, for example, U.S. Pat. No. 5,854,033 at FIG. 11 thereof).

In accordance with the processes disclosed herein, one or more primers can attach to a TS-DNA product through a chemical linkage selected from the group consisting of hybridization, a covalent bond or formation of a polynucleotide triplex.

The poly-primed rolling circle amplification (PPRCA) of the present invention offers an improvement over linear or hyperbranched rolling circle amplification in that the kinetics are truly exponential in nature (with products being formed, or amplified, in geometrically increasing amounts from multiple starting sites) while avoiding strand displacement by using an additional set of primers (P2) that bind to an RCA TS-DNA product and, in at least one embodiment, to additional amplification target circles to yield additional tandem sequence DNA products that may or may not be similar to the original or primary TS-DNA product. Thus, the method of the present invention effectively decouples the primary and all later rounds of amplification.

Put differently, in other RCA methods, the secondary DNA amplification is derived from primers that initiate DNA synthesis using the initial TS-DNA product as template so that all secondary TS-DNA is necessarily structurally related to the sequence of the initial, or primary, TS-DNA product, and so strand displacement is necessitated. In the polyprimed RCA of the present invention, a secondary primer (or P2) can have separate segments, one that binds to the primary TS-DNA (for anchorage purposes only) and an additional segment that serves as a primer while being complementary to a completely distinct amplification target circle (ATC) so that all of the secondary, and possibly tertiary, quaternary, and higher order rounds of amplification, amplify the ATCs that bind to the P2 primers, or the P3 primers, or the P4 primers, etc. Using the PPRCA methodology disclosed herein it is possible to generate as many stages of amplification as is desired, providing the reactions conditions permit, wherein each stage of amplification replicates a potentially different set of ATCs, each set differing in nucleotide sequence and wherein each stage generates a new TS-DNA that is its own concatamer of tandem repeats, each based on the set of ATC templates that it is being copied.

A sample embodiment of the methods of the present invention is described in FIG. 1, which shows a schematic for one embodiment of the polyprimed rolling circle amplification (PPRCA) method of the present invention. Here, an oligonucleotide primer (about 20–50 bases in length) with a region complementary to the amplification target circle (about 65–150 bases in length) (see A) and with a short non-complementary region. In B, the complementary region of the oligonucleotide primer (20–50 bases long) hybridizes specifically to the amplification target circle, with addition of enzyme, dNTPs, etc., as described for LRCA (C). D shows extension of the RCA primer with DNA polymerase displacing the earlier segment. In E, the second oligonucleotide primer (20–50 bases long) with a region identical to the target circle (16–50 bases long) and a non-complementary region (2–10 bases long) hybridizes to the tandemly repeated RCA product. In F, a second amplification target circle (about 70–150 bases in length) with a region complementary to the 3'-end of primer 2 hybridizes to primer 2 and initiates RCA from the 3'-end thereof (along the circular template). In some embodiments, the second amplification target circle may be identical, or similar, in sequence to the primary ATC. In G, the result is seen to be a series of linear RCA TS-DNA products formed from the linear rolling circle scaffold, thus affording exponential amplification. Methods according to the present invention can also employ further primer complementary sequences on the secondary strand to provide tertiary synthesis and further exponentiation of the amplified product.

In accordance with the present invention, the oligonucleotide primer (primer 1 or P1) acts as a rolling circle replication primer and is simply an oligonucleotide having sequence complementary to a "primer complement portion" an ATC. This sequence is referred to as the "complementary portion" of the primer P1. The complementary portion of an oligonucleotide primer (such as P1) and the primer complement portion of the amplification target circle can have any desired sequence so long as they are complementary to each other. Such sequence on P1 may not be complementary to some other portion of the amplification target circle or may be complementary to most of the sequence of the ATC the primer completely binds to said ATC, preferably with a small segment of the ATC not bound to the primer.

The complementary portion of the rolling circle replication (RCA) primers (P1) useful in the present invention can be any length that supports specific and stable hybridization between the primer and the primer complement portion. Generally this is 10 to 35 nucleotides long, but is preferably 16 to 20 nucleotides long.

The oligonucleotide primers of the present invention may, as described above, have segments non-complementary to a portion, or all, of the ATC. Such non-complementary portions, when present, serve to facilitate strand displacement during RCA. The non-complementary portion of such oligonucleotide primers may be any length, but is generally 1 to 100 nucleotides long, and preferably 4 to 8 nucleotides long.

Amplification target circles (ATC) useful in the processes of the present invention are circular single-stranded DNA molecules, generally containing between 40 to 1000 nucleotides, preferably between about 50 to 150 nucleotides, and most preferably between about 50 to 100 nucleotides. The ATCs useful in the processes disclosed herein may have functionally different portions, or segments, making them particularly useful for different purposes. At least one such portion will be complementary to one or more oligonucleotide primers.

For ATCs useful in the processes disclosed herein, the primer complement portion is a required element of an amplification target circle. Other portions are optional and can be selected to have an arbitrarily determined sequence. It is preferred that ATCs do not have any sequences that are self-complementary, a condition met if there are no complementary regions greater than about six nucleotides long without a mismatch or gap. ATCs useful in the process have been described in Lizardi, U.S. Pat. No. 5,854,033 (the disclosure of which is hereby incorporated by reference in its entirety) and in Lizardi et al, Mutation Detection and Single-Molecule Counting Using Isothermal Rolling Circle Amplification, *Nature Genetics*, 19, 225–232 (1998).

In some embodiments, one of the oligonucleotide primers may have, for example, 2 arms (i.e., is a 3'-5'-3'oligonucleotide, with one arm optionally providing target recognition and another that optionally acts as a primer for initiation of RCA with a circle). An example of such "bipolar" (3'-5'-3') oligonucleotides, with sources thereof, is shown in Lizardi et al (1998, supra). Such bipolar primers find use for attachment to a solid substrate, such as where primer P1 used herein is a bipolar primer. Unlike with presently available RCA methods, such bipolar primers are useful in the methods of the present invention because the present invention avoids primer displacement. Thus, if such primers were employed as, for example, P2 primers in exponential or hyperbranched RCA (see Lizardi et al (1998) for a description of the latter procedure) the strand displacement action would fail because there would be no 5'-end to be displaced (i.e., the result would be primers bound to the TS-DNA in the wrong orientation because of the bipolarity of the primers) and the result would be no amplification. In such RCA methods, bipolar primers find use only as P1 primers. In the processes of the present invention, any of the primers used may be bipolar.

In PPRCA, amplification occurs with each primer, thereby forming a concatamer of tandem repeats (i.e., a TS-DNA) of segments complementary to the primary ATC (or ATC 1) being replicated by each primer. Bipolar primers therefor are available for use as P2 primers because the method of the present invention avoids strand displacement and, since the bipolar primers have a 3'-OH at each end, they are automatically in the proper orientation for use as a primer for additional stages of amplification. In addition, because the bipolar primers have a 3-OH at each end, they serve to curtail any strand displacement that might otherwise occur. Further, because of the presence of a 3'-OH at each end of the bipolar primer, the TS-DNA and secondary, or higher order, ATCs (ATC 2, ATC 3, ATC 4, and so on) complementary sequences can be arranged in any configuration within the primer sequence.

Depending upon the size of the amplified circle, and the DNA polymerase used, PPRCA achieves an extremely high degree of amplification (and sensitivity) that can be optimized for the numbers of circles (often determined ad hoc for the particular primers and target sequences to be employed), DNA polymerases, dNTPs and $Mg^{2+}$. The product of this reaction is then optionally decorated and detected (for example, using a fluor-tagged oligonucleotide, or other tagged oligonucleotide, of sequence identical to a region of the circle).

To aid in detection and quantitative evaluation of nucleic acids amplified using RCA, detection labels can be directly incorporated into amplified nucleic acids or can be coupled to detection molecules. Such a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples include radioactive isotopes, fluorescent molecules, phosphorescent molecules, enzymes, antibodies, and ligands.

Examples of suitable fluorescent labels include fluorescein, 5,6-carboxymethyl fluorescein, Texas red, nitrobenz-2-oxa-1,3-diazol-4-yl (NB coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, Oreg. and Research Organics, Cleveland, Ohio.

Labeled nucleotides are preferred form of detection label since they can be directly incorporated into the products of RCA during synthesis. Examples of detection labels that can be incorporated into amplified DNA include nucleotide analogs such as BrdUrd (Hoy and Schimke, *Mutation Research*, 290:217–230 (1993)), BrUTP (Wansick et al., *J. Cell Biology*, 122:283–293 (1993)) and nucleotides modified with biotin (Langer et al., *Proc. Natl. Acad. Sci. USA*, 78:6633 (1981)) or with suitable haptens such as digoxygenin (Kerkhof, *Anal. Biochem.*, 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label is Biotin-16-uridine-5'-triphosphate (Biotin-16-dUTP, Boehringher Mannheim).

Thus, in accordance with the present invention, reporter molecules may include a member selected from the group consisting of biotin, digoxigenin, hapten, an enzyme, and a mass tag or any combination of these, either as part of the same primer or TS-DNA or as part of separate primers or TS-DNAs. Thus, this could comprise separate DNAs, either primers, ATCs or TD-DNA products wherein one or more such structures are tagged, each with a different type of tag or a different tag of the same type or separate but identical tags. For example, one structure could be tagged with a mass tag and the other with a fluorescent tag, or one with a mass tag and the other with a different mass tag, or each coupled to the same mass tag. Additionally, two or more polynucleotides, or oligonucleotides within the present invention may be tagged in this way within the same reaction mixture or within the same series of reactions as disclosed according to the methods of the present invention.

In another embodiment, the invention features the use of a reporter molecule attached to a dNTP wherein said reporter molecule is incorporated into tandem sequence DNA by the action of the polymerase. Such reporter molecules may be any that are described in the art. For example, haptens, such as, digoxigenin, biotin, estradiol, fluorescein, or other have been conjugated to deoxy-nucleotide triphosphates and employed as substrates for polymerases for incorporation into high molecular weight DNA. Similarly, modified nucleotides such as N7- or N9-deazapurine nucleotide or 2' fluoro 2' deoxy nucleotides, including so-called universal nucleotides, have been employed for enzymatic DNA synthesis. This invention is equally adaptable to a variety of detection methods for identification and quantification of the tandem sequence DNA produced by the process of this invention. Examples of such detection methods include, but are not limited to, fluorescence detection, such as in a microscope or fluorescence scanner, enzymatic detection, or MALDI-TOF mass spectroscopy. Mass tagged dideoxy NTPs have been described in (Nucleic Acids Res Jun. 1, 1998;26(11):2827–8) and is hereby incorporated by reference.

In other embodiments, the invention describes a reactive molecule that binds to the reporter molecule and aids in detection of the tandem sequence DNA. In alternative embodiments, said binding of reactive molecule to reporter molecule is reversible. Examples of reversible molecular interactions described in the art include: enzyme:substrate and antibody:hapten interactions, metal ion, temperature or cofactor dependent interactions involving proteins and/or DNA complexes, metal ion:chelator interactions, and so on. Examples of enzymes that can be employed in the invention are known to those skilled in the art, and include, horseradish peroxidase, alkaline phosphatase, and luciferase.

In accordance with the present invention, detection of reporter molecules can be achieved by binding said reporter molecules with a conjugate that contains a protein portion that binds to and recognizes the reporter and a DNA portion that may contain additional detection labels. In alternative embodiments, said DNA portion may contain one or more detection tags or serve as an initiator for additional polymerase extension reactions. In alternative embodiments, said protein or proteins comprise double-strand or single strand binding protein or an aptamer. Aptamers are single-stranded oligonucleotides that bind to target molecules. They have been described in numerous publications, e.g., Mol Diagn 1999 December;4(4):381–8.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrates like CSPD® (disodium 3-(4-methoxyspiro {1,2-dioxetane-3-2'-(5'-chloro)tricyclo[decan]-4-yl)phenyl phosphate); CDP-Star® (disodium 2-chloro-5-(4-methoxyspiro {1,2-dioxetane-3-2'-(5'-chloro)tricyclo [3.3.1.1$^{3,7}$]decan}-4-yl) phenyl phosphate) and AMPPD® (disodium 3-(4-methoxyspiro {1,2-dioxetane-3-2'-tricyclo [3.3.1.1$^{3,7}$] phenyl phosphate) (all available from Tropix, Inc.—see: www.tropix.com).

Molecules that combine two or more of these detection labels are also considered detection labels. Methods for detecting and measuring signals generated by detection labels are known to those of skill in the art. For example, radioactive isotopes can be detected by scintillation counting or direct visualization and fluorescent molecules can be detected with fluorescent spectrophotometers. Such detection molecules interact with amplified nucleic acid and have one or more detection labels are coupled.

Examples of molecules for use in detecting any of the tandem sequence DNA products formed according to the invention include, but are not limited to, decorators, or decorating agents, including hybridization probes, any of the fluorescent agents disclosed herein, ligand binding molecules (such as avidin), antibodies, FKBP fold binding molecules (such as rapamycin), enzymes, receptors, nucleic acid binding proteins (such as transcription factors), ribosomal or other RNA binding proteins, affinity agents (such as aptamers, which are nucleic acids with affinity for small molecule ligands [See: Marshall et al, *Current Biology*, 5, 729–734 (1997) for a review], and other agents known to those skilled in the art and suitable for conjugation with an RCA primer or detection tag.

One embodiment of the present invention is described schematically in FIG. 1 (step E). Here, secondary DNA primers (P2) bind to the tandem sequence DNA product. Such primers commonly have a first portion, or 5' portion, having a sequence located at or near the 5'-end of said primer P2 and which is complementary to a portion, or segment, of the tandem sequence DNA being produced by the initial linear RCA. The secondary primers also commonly possess a second portion, or 3'-portion, located at or near the 3'-end of said primer P2, and which have a sequence that is complementary to a portion of an amplification target circle (ATC), which ATC may have a sequence the same as, similar to, or different from the ATC used in the initial step of this process. The TS-DNA complementary portion of the secondary primer may be complementary to any sequence in TS-DNA. However, it is preferred that it not be complementary TS-DNA sequence matching the rolling circle replication primer in order to prevent hybridization of the primers to each other. The complementary portion of a secondary DNA primer (P2) can be any length that supports specific and stable hybridization between the primer and its complementary sequence, either in TS-DNA or in an ATC. Generally this is 12 to 35 nucleotides long, but is preferably 18 to 25 nucleotides long.

Oligonucleotide primers and ATCs useful in the present invention can be synthesized using established oligonucleotide synthesis methods. Methods of synthesizing oligonucleotides are well known in the art. Such methods can range from standard enzymatic digestion followed by nucleotide fragment isolation (see for example, Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols, in Methods in Molecular Biology*, Vol. 62, (Tuan, ed., Humana Press, Totowa, N.J., 1997), the disclosures of which are hereby incorporated by reference) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques*

8:674–678 (1990), and Rychlik et al., *Nucleic Acids Res.* 18:6409–6412 (1990).

The ATCs of the present invention, or even the oligonucleotide primers, can be used in a form in which they are attached, by whatever means is convenient, to some type of solid support. Attachment to such supports can be by means of some molecular species, such as some type of polymer, biological or otherwise, that serves to attach said primer or ATC to a solid support so as to facilitate detection of tandem sequence DNA produced by rolling circle amplification using the methods of the invention (i.e., PPRCA).

Such solid-state substrates useful in the methods of the invention can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide glass, polysilicates, polycarbonates, Teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide or a microtiter dish (for example, the standard 96-well dish). For additional arrangements, see those described in U.S. Pat. No. 5,854, 033.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994). A preferred method of attaching oligonucleotides to solid-state substrates is described by Guo et al., *Nucleic Acids Res.* 22:5456–5465 (1994).

DNA polymerases useful in the rolling circle replication step of RCA must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ATC. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ-29 DNA polymerase (U.S. Pat. Nos. 5,198, 543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), VENT.RTM. DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), and T4 DNA polymerase holoenzyme (Kaboord and Benkovic, *Curr. Biol.* 5:149–157 (1995)). φ-29 DNA polymerase is most preferred. Equally preferred polymerases include T7 native polymerase and Bst polymerase.

Strand displacement during RCA can be facilitated through the use of a strand displacement factor, such as helicase. In general, any DNA polymerase that can perform rolling circle replication in the presence of a strand displacement factor is suitable for use in the processes of the present invention, even if the DNA polymerase does not perform rolling circle replication in the absence of such a factor. Strand displacement factors useful in RCA include BMRF1 polymerase accessory subunit (Tsurumi et al., *J. Virology* 67(12):7648–7653 (1993)), adenovirus DNA-binding protein (Zijderveld and van der Vliet, *J. Virology* 68(2) :1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22) :10665–10669 (1994)), single-stranded DNA binding proteins (SSB; Rigler and Romano, *J. Biol. Chem.* 270:8910–8919 (1995)), and calf thymus helicase (Siegel et al., *J Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in Lizardi (U.S. Pat. No. 5,854,033, e.g., Example 1 therein).

In accordance with the foregoing, the present invention relates to a process for selectively amplifying nucleic acid sequences, comprising:

(a) mixing at least one single stranded non-circular first-stage oligonucleotide primer (P1) and at least one single stranded first-stage amplification target circle (ATC1) to produce a primer-ATC sample mixture;

(b) incubating said primer-ATC1 sample mixture under conditions that promote hybridization between the oligonucleotide primer and the amplification target circle to form a hybridized primer-ATC1 sample mixture and allowing sufficient time to pass for hybridized primer-ATC1 complexes to form;

(c) mixing a DNA polymerase and at least two deoxynucleotide triphosphates with said hybridized primer-ATC1 sample mixture to produce a polymerase-primer-ATC1 sample mixture and incubating the polymerase-primer-ATC1 mixture under conditions that promote replication of the amplification target circles to form a primary tandem sequence DNA (TS-DNA);

(d) adding to said polymerase-primer-ATC1 mixture at least one second-stage primer oligonucleotide (P2) comprising a first portion, or segment, having a sequence complementary to one or more sequences present in said primary TS-DNA and a second portion, including a free 3'-OH end, having a sequence not complementary to said primary TS-DNA, under conditions promoting hybridization of said first portion of P2 to said primary TS-DNA thereby forming a TS-DNA-P2 complex;

(e) adding one or more second-stage amplification target circles (ATC2) to the mixture in (d) under conditions promoting hybridization of said ATC2 to said second portion of P2 to form a tandem sequence-P2-ATC mixture, wherein replication of the amplification target circles of (e) results in formation of additional, or, in this case, secondary tandem sequence DNA (or 2°-TS-DNA).

As disclosed herein according to the present invention, the term "first-stage" refers to the initial step of a linear RCA reaction to form primary tandem-sequence DNA.

Also in accordance with the present invention, the methods disclosed herein are in no way limited to one level of amplification and additional stages are easily facilitated. Thus, the present invention further relates to additional rounds, or stages, of amplification with additional stage primers and amplification target circles being employed and the only limit being found in the inclinations and needs of the user.

In accordance therewith, the present invention, in addition to the already recited process for amplification of selected DNA sequences, further comprises the additional steps of:

(f) adding to said polymerase-primer-ATC2 mixture at least one third-stage primer oligonucleotide (P3) comprising a first portion, or segment, having a sequence complementary to one or more sequences present in said secondary TS-DNA and a second portion, including a 3'-OH end, having a sequence not complementary to said secondary TS-DNA, under conditions promoting hybridization of said first portion of P3 to said secondary TS-DNA thereby forming a TS-DNA-P3 complex;

(g) adding one or more third-stage amplification target circles (ATC3) to the mixture in (f) under conditions promoting hybridization of said ATC3 to said second portion of P3 to form a tandem sequence-P3-ATC3 mixture, wherein replication of the amplification target circles of (f) results in formation of tertiary tandem sequence DNA.

For an additional stage or level of amplification, the processes of the present invention further comprises the additional steps of:

(h) adding to said polymerase-primer-ATC3 mixture at least one fourth-stage primer oligonucleotide (P4) comprising a first portion, or segment, having a sequence complementary to one or more sequences present in said tertiary TS-DNA and a second portion, including a 3'-OH end, having a sequence not complementary to said tertiary TS-DNA, under conditions promoting hybridization of said first portion of P4 to said tertiary TS-DNA thereby forming a TS-DNA-P4 complex;

(i) adding one or more fourth-stage amplification target circles (ATC4) to the mixture in (h) under conditions promoting hybridization of said ATC4 to said second portion of P4 to form a tandem sequence-P4-ATC4 mixture, wherein replication of the amplification target circles of (h) results in formation of quaternary tandem sequence DNA.

Of course, this can be continued round after round to levels well beyond those expressly described herein.

In one such embodiment, the present invention relates to a process such as that just described wherein the conditions of step (c) (above) that promote replication include the presence in said mixture of a dNTP substrate bound to a first reporter molecule and wherein said first reporter molecule is thereby incorporated into said tandem sequence DNA. In such an embodiment, the primer oligonucleotide P2 may be bound to a first reactive molecule capable of binding to said first reporter molecule.

The process of the present invention also include embodiments wherein the dNTPs used to extend primer P2 are bound to a second reporter molecule such that said second reporter molecule becomes incorporated into the secondary tandem sequence DNA. In this embodiment, the primer oligonucleotide P3 may be bound to a second reactive molecule capable of binding to said second reporter molecule.

In a further embodiment, the processes of the present invention include situations wherein the dNTPs used to extend primer P3 are bound to a third reporter molecule such that said third reporter molecule becomes incorporated into the tertiary tandem sequence DNA described above. In a further such embodiment, the primer oligonucleotide P4 may be bound to a third reactive molecule capable of binding to said third reporter molecule.

This process can, of course, continue for any number of desired rounds of PPRCA as described herein.

In any of the embodiments of the present invention, dNTPs are members selected from the group consisting of dUTP, dCTP, dATP, dGTP, a naturally occurring dNTP different from the foregoing, an analog of a dNTP, and a dNTP having a universal base.

The processes disclosed according to the present invention are highly useful for multiplexing applications, where multiple target sequences and primers are to be used. At the outset, primers (P1) may differ from each other as may all or part of the sequences of the amplification target circles (ATC1). Here, the use of a digit after the primer or ATC indicates a stage of amplification in the multistage, or polyprimed RCA (or PPRCA) of the present invention. Thus, the primers and amplification target circles may differ within the population used in a given stage, or may be the same in a given stage but differ from stage to stage. Further, primers beyond P1 (i.e., P2 onward) all have at least two portions, or segments, or sequences, one of which, denoted a first portion, is complementary to the TS-DNA synthesized in the earlier steps of the particular process being carried out, and serve as probes for attachment to the TS-DNA synthesized in such earlier steps. The later primers also typically have a second portion, usually contiguous to the first, with the second also typically including a 3'-OH group and denoting a 3'-end of said primer, wherein said second portion is complementary to at least one portion of an amplification target circle. Thus, the first and second portions of said primers will commonly be of different structure, or sequence, although this is not an absolute requirement of the methods disclosed herein.

The multi-stage primers of the present invention may be the same or different in structure either at a given stage or between stages. The same is true for the amplification target circles used herein.

In a specific embodiment, the primer oligonucleotides of a given stage may all have the same structure (i.e., the same sequence). Where this is the case, the amplification target circles of this same stage will likewise have the same, or similar, structures since they are to be complementary to the primers. Because the ATCs bind only to the second portion of primer oligonucleotides beyond P1, it is possible for primers in a given stage to have identical first portions but have different second portions and thus bind to the same tandem sequence DNA but to separate populations of ATCs because of the difference in sequence of their second portions. Because each round of amplification occurs using only the second portion of the primer and an ATC, with the first portion optionally remaining bound to the TS-DNA of the previous round, there is no need for strand or primer displacement in the methods of the present invention.

The processes according to the present invention may further comprise detecting the presence of tandem sequence DNA. Such detection may include, but is not limited to, a process wherein the conditions of step (c) above that promote replication include the presence in the mixture of a dNTP substrate bound to a reporter molecule and wherein said reporter molecule is thereby incorporated into said tandem sequence DNA. A preferred reporter molecule is biotin and the dNTP can include any of the dNTPs, including dATP, dGTP, dTTP, dCTP, and dUTP. Of course, each round of amplification further enhances the ability to detect any given target sequence, especially where multiple target sequences are to be detected simultaneously using highly specific, but separate, detector or reporter molecules.

The present invention further relates to a process as described above, but further comprising a primer oligonucleotide, as in step (d), or (f), or (h), wherein said primer oligonucleotide is bound to a reactive molecule capable of binding to said reporter molecule. In one embodiment of the present invention, said reactive molecule is a conjugate, with a preferred embodiment being an anti-biotin-DNA conjugate.

The present invention further relates to a process wherein the conditions, described above, that promote replication (such as steps (e), or (g), or (i) in the methods described herein) include the presence in the mixture of a dNTP substrate bound to a reporter molecule and wherein said reporter molecule is thereby incorporated into the tandem sequence DNA produced by the process of the invention. In a preferred embodiment, said reporter molecule is Cy5 or Cy3. Here, again, the dNTP may include any of the common dNTPs, including dUTP.

Figure 2:
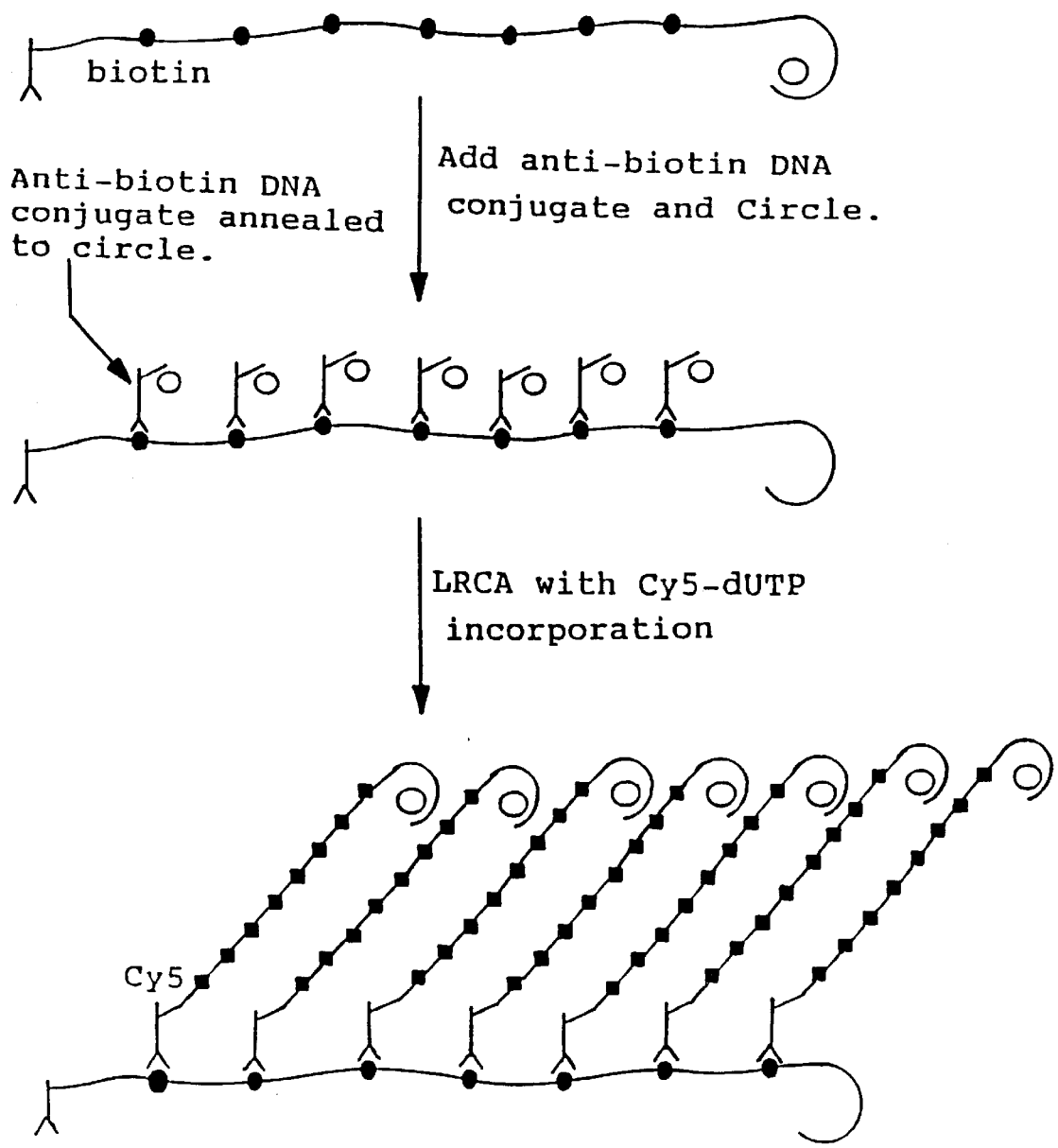
FIG. 2 shows a sample PPRCA run using an anti-biotin DNA conjugate. Here, incorporation of biotin (or other suitable hapten) as a conjugate with dUTP (or other suitable deoxynucleoside triphosphate) on the initial TS-DNA product results in product from immobilized product oligonucleotides. Added antibody-DNA conjugates bind to the TS-DNA and thereby give rise to increase detection with the bound conjugates then serving as the platform for a second RCA reaction to detect the primary amplified product. As shown for step 2 in the figure, a second level of detection is afforded by addition to the multiple tandem sequence DNA product of primers possessing a separate and different signal detection molecule or reporter molecule, here Cy5, which affords increased signal amplification for an additional round of RCA. An important aspect of the present invention is that it eliminates the strand displacement of hyperbranching primers during polymerase read-through used in exponential RCA.
Figure 3:
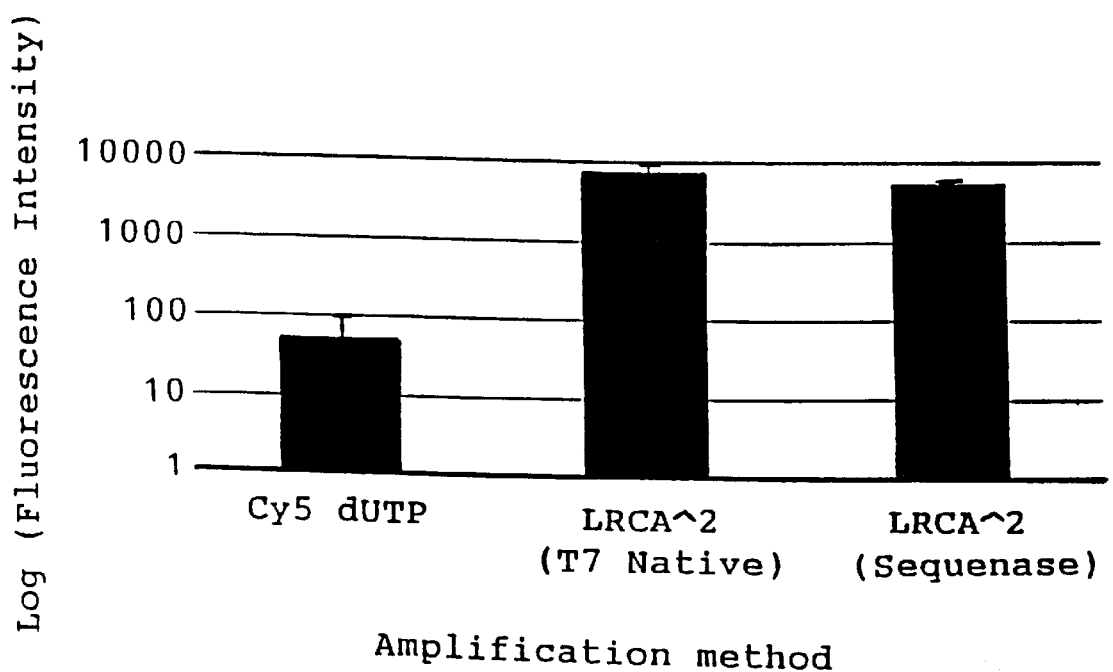
FIG. 3 is a plot showing the increase in signal intensity afforded by the PPRCA processes of the present invention (here using an anti-biotin conjugate system). The signal intensity with PPRCA is about 100-fold greater than conventional linear rolling circle amplification (LRCA control in column 1 on the left of the figure) methods (using Cy5-dUTP incorporation).
Figure 4:
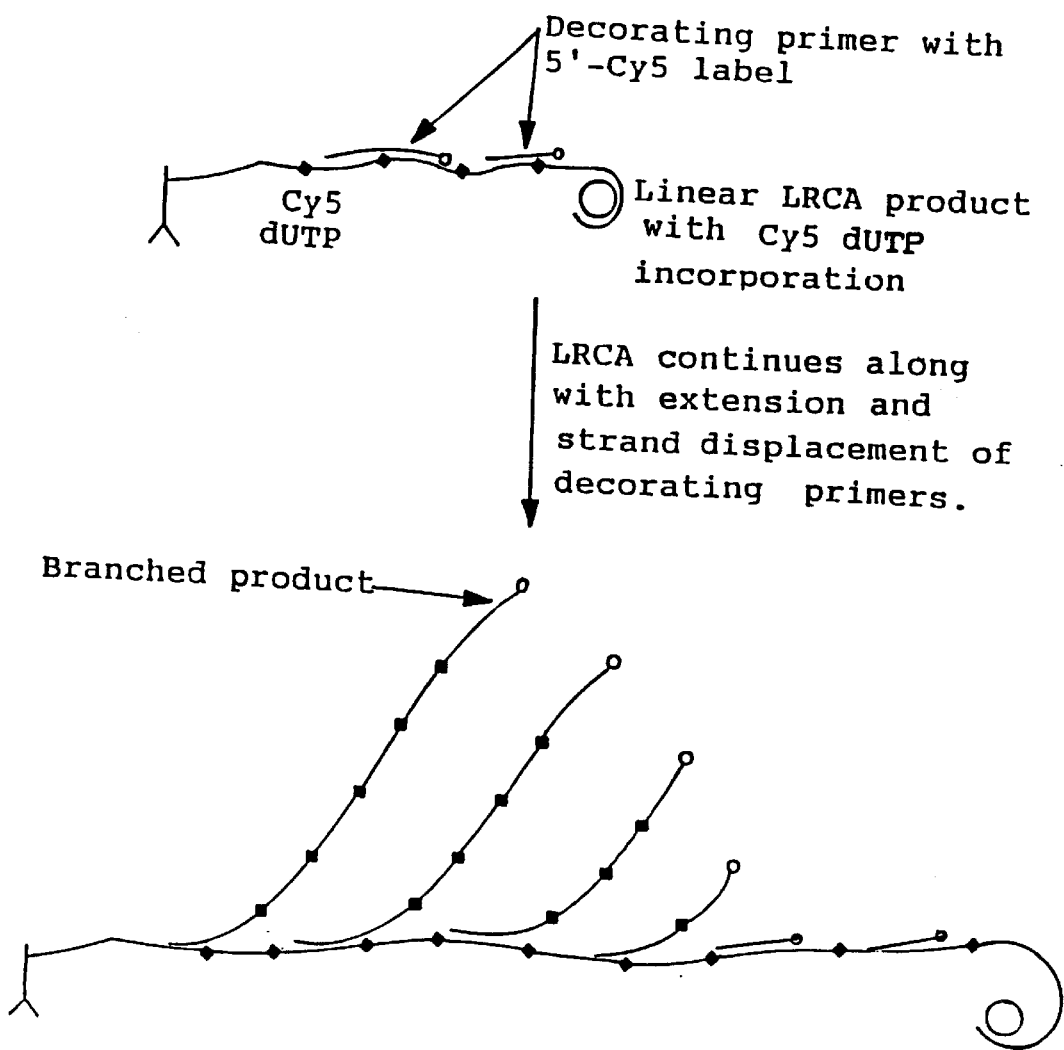
FIG. 4 shows branched RCA using fluor-labeled decorating primers and fluor-dUTP incorporation into the tandem sequence DNA. The decorating primers are annealed directly to the RCA product and extended by DNA polymerase. Incorporation of fluor-labeled dUTP allows for increased signal intensity by incorporation of the modified nucleotide in both the initial TS-DNA product and the branched sequence that is formed by extension and strand displacement of the decorating primers but wherein the dUTP bound to TS-DNA in the first RCA is different from that bound in the second and any higher stages.

In one embodiment of the present invention, as described in FIG. 2, a sample PPRCA is run using an anti-biotin DNA conjugate. Here, incorporation of biotin (or other suitable hapten) as a conjugate with dUTP (or other suitable deoxynucleoside triphosphate) on the initial TS-DNA product results in product from immobilized product oligonucleotides. Added antibody-DNA conjugates bind to the TS-DNA and thereby give rise to increased signal detection with the bound conjugates then serving as the platform for a second RCA reaction to detect the primary amplified product. As shown for step 2 in the figure, a second level of detection is afforded by addition to the multiple tandem sequence DNA product of primers possessing a separate and different signal detection molecule or reporter molecule, here Cy5, which affords increased signal amplification for an additional round of RCA. An important aspect of the present invention is that it eliminates the strand displacement of hyperbranching primers during polymerase read-through used in exponential RCA.

In one such embodiment, target nucleotides to be detected by amplification are incorporated into single stranded circular DNAs amplified together as part of the same ATC. These same ATCs can then be used in each successive stage of amplification and each of the target sequences is amplified simultaneously with other target sequences.

In addition to the foregoing, the primer oligonucleotides of the present invention may be branched chains so that a single primer contains one or more of the same or different sequences at the end of a number of branch points, each complementary to the same or different amplification target circles, most advantageously with one end of said branched oligonucleotide primers, such as where the latter are dendrimers, attached to some type of solid support, such as the solid supports described hereinabove. Use of such branched chain primer oligonucleotide thereby provides an added level of amplification using the methods of the present invention.

In carrying out the methods of the present invention, said circular DNA may be derived from a padlock probe and a portion of a target sequence is derived from a padlock gap-fill in procedure. [See: Nilsson et al., "Padlock Probes: Circularizing Oligonucleotides for Localized DNA Detection", Science, 265:2085–2088 (1994), Lizardi, U.S. Pat. No. 5,854,033]

As before, these embodiments of the present invention may further comprise detecting the tandem sequence DNA produced by the process of the invention. Here, again, in detecting said product the conditions of step (c) that promote replication include the presence in said mixture of a dNTP substrate, including, for example, dUTP, bound to a reporter molecule and wherein said reporter molecule is thereby incorporated into said tandem sequence DNA. In a particular embodiment, the reporter molecule is biotin.

The present invention may further comprise this just described embodiment wherein the primer oligonucleotide of step (d) is bound to a reactive molecule capable of binding to said reporter molecule. In preferred embodiments, this reactive molecule is a conjugate, especially an anti-biotin-DNA conjugate. In a most preferred embodiment, the reporter molecule is Cy5.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

PPRCA Using an Anti-biotin DNA Conjugate

Fifty nM DNA circles in PBS were annealed to immobilized primers on glass slide. The slide was washed for 1 minute in 40 mM Tris pH 7.5, 25 mM NaCl, 10 mM $MgCl_2$ and spun dry in clinical desktop centrifuge for 1 minute at 1000 rpm.

The following PPRCA reaction mixture was used: 1×Sequenase Reaction Buffer 0.4 mM dATP, 0.4 mM dCTP, 0.4 mM dGTP, 0.3 mM dTTP, 0.1 mM biotin-16-dUTP, 0.01 U/$\mu$l T7 DNA Polymerase, 0.03 ug/ml SSB, 0.05 uM decorating oligo (5'-Cy5 and 3'-Cy5).

The PPRCA reaction mixture was then added to a glass slide and incubate at 37° C. for 30 minutes. About 50 nM Circle were pre-annealed to 1 ng/ul anti-biotin DNA conjugate in PBS, 0.05% Tween 20, 1 mM EDTA at 37° C. for 30 minutes. The slide was then washed for two minutes in PBS, 0.05% Tween 20 at room temperature and rinsed in PBS/0.05% Tween 20.

A pre-annealed mixture of circles and anti-biotin DNA conjugate was then added to the slide and incubated at 37° C. for 30 minutes, the slide was washed twice for two minutes in PBS, 0.05% Tween 20.

The following PPRCA reaction mixture was prepared: 1× Sequenase Reaction Buffer, 0.4 mM dATP, 0.4 mM dCTP, 0.4 mM dGTP, 0.3 mM dTTP, 0.1 mM Cy5-dUTP, 0.01 U/ul T7 DNA Polymerase, 0.03 ug/ml SSB (single stranded binding proteins).

This mixture was added to the slide and incubated at 37° C. for 30 minutes. The slide was then washed twice for two minutes in 2×SSC/0.05% Tween 20 at room temperature and rinse in 1×SSC and spun-dry in clinical desktop centrifuge at 1000 rpm for 1 minute.

EXAMPLE 2

PPRCA with Decorating Primers

About 50 nM circles in PBS were annealed to immobilized primers on a glass slide and the slide washed for 1 minute in 40 mM Tris pH 7.5, 25 mM NaCl, 10 mM MgCl$_2$ and then spun dry in clinical desktop centrifuge for 1 minute at 1000 rpm.

The following PPRCA reaction mixture was prepared: 1×Sequenase Reaction Buffer, 0.4 mM dATP, 0.4 mM dCTP, 0.4 mM dGTP, 0.3 mM dTTP, 0.1 mM Cy5-dUTP, 1 U/ul Sequenase, 0.03 ug/ml SSB (single-strand binding protein), and 0.05 uM decorating primer (5'-Cy5).

This reaction mixture was then added to a glass slide and incubated at 37° C. for 30 minutes. The slide was then washed twice for two minutes in 2×SSC/0.05% Tween 20 at room temperature and rinsed in 1×SSC. It was spun dry as previously described.

What is claimed is:

1. A process for detecting nucleic acid sequences comprising:
   (a) contacting a single stranded non-circular oligonucleotide primer with an amplification target circle (ATC), said ATC comprising a segment complementary to at least one segment of said primer and wherein said at least one segment includes the 3'-terminus of said primer, under conditions promoting hybridization of said primer with said ATC to form a primer-ATC complex,
   (b) contacting said complex of (a) with a rolling circle amplification (RCA)-promoting enzyme under conditions promoting rolling circle amplification of said ATC from the 3'-terminus of said primer, wherein said conditions include the presence of a dNTP substrate bound to a reporter molecule, to form a tandem sequence DNA (TS-DNA) that incorporates said reporter molecule,
   (c) contacting said TS-DNA with a plurality of primers wherein said primers are bound at their 5'-terminus to a reactive molecule that binds to said reporter molecule and wherein said primers comprise a segment not complementary to said TS-DNA of (b),
   (d) contacting said plurality of primers with a plurality of ATCs each comprising a segment complementary to a segment of said plurality of primers of (c) wherein said segment of said plurality of primers includes the 3'-terminus thereof, under conditions promoting rolling circle amplification of said plurality of primers to form additional TS-DNA,
   (e) repeating steps (c) and (d) n times where n has a value of 0 or higher,
   (f) detecting the presence of said TS-DNA.

2. The process of claim 1 wherein n has a value of 1, 2 or 3.

3. The process of claim 1 wherein n has a value greater than 3.

4. The process of claim 1 wherein said plurality of ATCs of (d) are identical.

5. The process of claim 1 wherein said ATC of (a) further comprises a segment not complementary to said primer of (a).

6. The process of claim 1 wherein said plurality of ATCs of (d) each further comprises a segment not complementary to said plurality of primers of (d).

7. The process of claim 1 wherein said RCA-promoting enzyme is a member selected from the group consisting of bacteriophage φ-29 DNA polymerase, phage M2 DNA polymerase, phage φ-PRD1 DNA polymerase, VENT.RTM. DNA polymerase, Klenow fragment of DNA polymerase I, T5 DNA polymerase, PRD1 DNA polymerase, and T4 DNA polymerase holoenzyme, T7 native polymerase and Bst polymerase.

8. The process of claim 1 wherein said reporter molecule is selected from the group consisting of biotin, digoxigenin, hapten, an enzyme, a mass tag and a combination of these.

9. The process of claim 1 wherein said reporter molecule is Cy3 or Cy5.

10. The process of claim 1 wherein said reporter molecule is a fluorophore.

11. The process of claim 1 wherein said reactive molecule is selected from the group consisting of an enzyme and a conjugate.

12. The process of claim 11 wherein said conjugate comprises a member selected from the group consisting of anti-biotin-DNA, anti-digoxigenin-DNA, a double stranded polynucleotide binding protein, a single stranded polynucleotide binding protein and an aptamer.

13. The process of claim 12 wherein said polynucleotide is a DNA.

14. The process of claim 11 wherein said primers are from 2 to 15 nucleotides in length.

15. The process of claim 11 wherein at least one primer is bipolar.

16. The process of claim 11 wherein at least one primer is attached to a solid support.

17. The process of claim 16 wherein said support is made of glass or plastic.

18. The process of claim 1 wherein said TS-DNA is detected by detecting the presence of a reporter molecule.

19. The process of claim 1 wherein said TS-DNA is detected by use of a decorator.

20. The process of claim 19 wherein said decorator is selected from the group consisting of hybridization probes, fluorophores, ligand binding molecules, antibodies, FKBP-fold binding molecules, enzymes, receptors, nucleic acid binding proteins, ribosomal binding molecules, antibodies and aptamers.

21. The process of claim 1 wherein said dNTPs are selected from the group consisting of dATP, dTTP, dGTP, dCTP, dUTP, a naturally occurring dNTP different from the foregoing, an analog of a dNTP, and a dNTP having a universal base.

22. A process for amplifying a selected nucleic acid sequence comprising:
   (a) contacting a single stranded non-circular oligonucleotide primer with an amplification target circle (ATC), said ATC comprising a segment complementary to at least one segment of said primer and a segment not complementary to said primer of (a) and wherein said at least one segment of said primer includes the 3'-terminus of said primer, under conditions promoting hybridization of said primer with said ATC to form a primer-ATC complex,
   (b) contacting said complex of (a) with a rolling circle amplification (RCA)-promoting enzyme under conditions promoting rolling circle amplification of said ATC from the 3-terminus of said primer, wherein said conditions include the presence of one or more deoxynucleoside triphosphates (dNTPs), to form a tandem sequence DNA (TS-DNA), (c) contacting said TS-DNA with a plurality of primers wherein said primers comprise a segment complementary to at least a portion of said TS-DNA and a segment not complementary to said TS-DNA, (d) contacting said plurality of primers with a plurality of ATCs each comprising a segment complementary to a segment of said plurality of primers of (c) that includes the 3'-terminus thereof, under conditions promoting rolling circle amplification of said plurality of primers to form additional TS-DNA, (e) repeating steps (c) and (d) n times where n has a value of 0 or higher, thereby amplifying said selected nucleic acid sequence.

23. The process of claim 22 wherein n has a value of 1, 2 or 3.

24. The process of claim 22 wherein n has a value greater than 3.

25. The process of claim 22 wherein said plurality of ATCs of (d) are identical.

26. The process of claim 22 wherein said plurality of ATCs of (d) each further comprises a segment not complementary to said plurality of primers of (d).

27. The process of claim 22 wherein said RCA-promoting enzyme is a member selected from the group consisting of bacteriophage φ-29 DNA polymerase, phage M2 DNA polymerase, phage φ-PRD1 DNA polymerase, VENT.RTM. DNA polymerase, Klenow fragment of DNA polymerase I, T5 DNA polymerase, PRD1 DNA polymerase, and T4 DNA polymerase holoenzyme, T7 native polymerase and Bst polymerase.

28. The process of claim 22 wherein said dNTPs are selected from the group consisting of dATP, dTTP, dGTP, dCTP, dUTP, a naturally occurring dNTP different from the foregoing, an analog of a dNTP, and a dNTP having a universal base.

29. The process of claim 22 wherein said conditions of step (b) include a dNTP bound to a reporter molecule and at least a portion of said plurality of primers are attached at their 5'-ends to a reactive molecule that reacts with said reporter molecule.

30. The process of claim 29 wherein said reporter molecule is selected from the group consisting of biotin, digoxigenin, hapten, an enzyme, a mass tag and a combination of these.

31. The process of claim 29 wherein said reporter molecule is Cy3 or Cy5.

32. The process of claim 29 wherein said reporter molecule is a fluorophore.

33. The process of claim 29 wherein said reactive molecule is selected from the group consisting of an enzyme and a conjugate.

34. The process of claim 33 wherein said conjugate comprises a member selected from the group consisting of anti-biotin-DNA, anti-digoxigenin-DNA, a double stranded polynucleotide binding protein, a single stranded polynucleotide binding protein and an aptamer.

35. The process of claim 34 wherein said polynucleotide is a DNA.

36. The process of claim 22 wherein said primers are from 2 to 15 nucleotides in length.

37. The process of claim 22 wherein at least one primer is bipolar.

38. The process of claim 22 wherein at least one primer is attached to a solid support.

39. The process of claim 38 wherein said support is made of glass or plastic.

40. The process of claim 22 wherein said TS-DNA is detected.

41. The process of claim 40 wherein said detection is accomplished by detecting the presence of a reporter molecule.

42. The process of claim 40 wherein said TS-DNA is detected by use of a decorator.

43. The process of claim 42 wherein said decorator is selected from the group consisting of hybridization probes, fluorophores, ligand binding molecules, antibodies, FKBP-fold binding molecules, enzymes, receptors, nucleic acid binding proteins, ribosomal binding molecules, antibodies, and aptamers.

* * * * *

UNITED STATES PATENT AND TRADEMARK OFFICE
CERTIFICATE OF CORRECTION

PATENT NO.     : 6,670,126 B1
DATED          : December 30, 2003
INVENTOR(S)    : Stephen Kingsmore, R. Steven Wiltshire and Jeremy P. Lambert It is certified that error appears in the above-identified patent and that said Letters Patent is hereby corrected as shown below:

Column 3,
Line 34, "a basic" should be -- abasic --

Column 4,
Line 2, "increase detection" should be -- increased signal detection --

Column 7,
Line 55, "3-OH" should be -- 3'-OH --

Column 8,
Line 19, "(NB" should be -- (NBD) --

Column 9,
Line 65, "labels are coupled" should be -- labels coupled --

Signed and Sealed this

Eighth Day of June, 2004

JON W. DUDAS
*Acting Director of the United States Patent and Trademark Office*